United States Patent [19]

Demerson et al.

[11] Patent Number: 4,585,877

[45] Date of Patent: Apr. 29, 1986

[54] PROCESS FOR PREPARING 1,8-DIETHYL-1,3,4,9-TETRAHYDROPYRANO(3,4-B)-INDOLE-1-ACETIC ACID, ETODOLAC

[75] Inventors: Christopher A. Demerson, Plainsboro; Leslie G. Humber, North Brunswick, both of N.J.

[73] Assignee: American Home Products Corporation, New York, N.Y.

[21] Appl. No.: 730,963

[22] Filed: May 6, 1985

[51] Int. Cl.[4] .................. C07D 491/052; C07D 209/12
[52] U.S. Cl. ...................................... 548/432; 548/508
[58] Field of Search ................................ 548/432, 508

[56] References Cited

U.S. PATENT DOCUMENTS

| | | |
|---|---|---|
| 3,939,178 | 2/1976 | Demerson et al. ............... 548/432 |
| 4,012,417 | 3/1977 | Demerson et al. ............... 548/432 |
| 4,021,451 | 5/1977 | Dobson et al. .................... 548/432 |

OTHER PUBLICATIONS

Demerson et al., J. Med. Chem., 19, 391 (1976).
I. I. Grandberg and T. P. Moskvina, Khim. Geterotsikl. Soedin., 1366 (1972), English translation.

*Primary Examiner*—Donald G. Daus
*Assistant Examiner*—Mary E. Ceperley
*Attorney, Agent, or Firm*—Walter Patton; John W. Routh

[57] ABSTRACT

A process for preparing 1,8-diethyl-1,3,4,9-tetrahydro[3,4-b]-indole-1-acetic acid (etodolac) is disclosed. Etodolac is a useful antiinflammatory and analgesic agent.

4 Claims, No Drawings

PROCESS FOR PREPARING 1,8-DIETHYL-1,3,4,9-TETRAHYDROPYRANO(3,4-B)-INDOLE-1-ACETIC ACID, ETODOLAC

BACKGROUND OF THE INVENTION

This invention relates to the process for the preparation of 1,8-diethyl-1,3,4,9-tetrahydropyrano[3,4-b]indole-1-acetic acid, also designated etodolac, disclosed as a potent antiinflammatory and analgesic compound in Demerson et al., U.S. Pat. No. 3,939,178.

Preparations for pyrano[3,4-b]indoles have been previously described in Demerson et al., U.S. Pat. Nos. 3,939,178 and 4,012,417 and in Demerson et al., J. Med. Chem., 19, 391 (1976).

Demerson et al., U.S. Pat. Nos. 3,939,178 and 4,012,417 disclose reaction of substituted tryptophols with keto ester to produce pyrano[3,4-b]indoles (see col. 9, lines 5 to 35). Etodolac is produced according to Example 477 of U.S. Pat. No. 4,012,417 by the reaction of 7-ethyltryptophol and the keto ester, ethyl propionylacetate, followed by alkaline hydrolysis. The 7-ethyltryptophol is produced by the reaction of 2-ethylphenylhydrazine with 4-hydroxybutyraldehyde.

Demerson et al., J. Med. Chem., 19, 391 (1976) also discloses the preparation of pyrano[3,4-b]indoles by the reaction of substituted tryptophols with keto esters. The 7-ethyltryptophol, necessary for the production of etodolac, is prepared by the reduction of ethyl 7-ethyl-3-indolylglyoxylate with LiAlH$_4$ (page 394, right column). The glyoxylate is produced by the reaction of 7-ethylindole with oxalyl chloride. The 7-ethylindole is produced from 2-ethylaniline in a thee step process. Demerson et al., also discloses the preparation of 7-cyclopropyltryptophol by the reaction of 2-cyclopropylphenylhydrazine hydrochloride with 2,3-dihydrofuran using the method described by I. I. Grandberg and T. P. Moskvina, Khim. Geterotsikl. Soedin., 1366 (1972).

SUMMARY OF THE INVENTION

According to the process of the present invention, etodolac is produced by the reaction of 7-ethyltryptophol with 3-methyoxy-2-pentenoic acid methyl ester at room temperature followed by alkaline hydrolysis. The 7-ethyltryptophol is produced directly by the reaction of 2-ethylphenylhydrazine hydrochloride with 2,3-dihydrofuran. The 3-methoxy-2-pentenoic acid methyl ester is produced by the reaction of methyl propionylacetate with trimethyl orthoformate in the presence of sulfuric acid. With the exception of an optional short heating period in the reaction of 2-ethylphenylhydrazine with 2,3-dihydrofuran, and the hydrolysis of the etodolac ester to etodolac in the final step, all the steps are carried out at or below room temperature. The process of the present invention is illustrated by the following scheme.

PROCESS FOR THE PREPARATION OF ETODOLAC

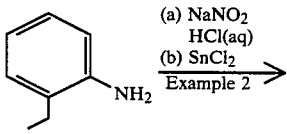

-continued
PROCESS FOR THE PREPARATION OF ETODOLAC

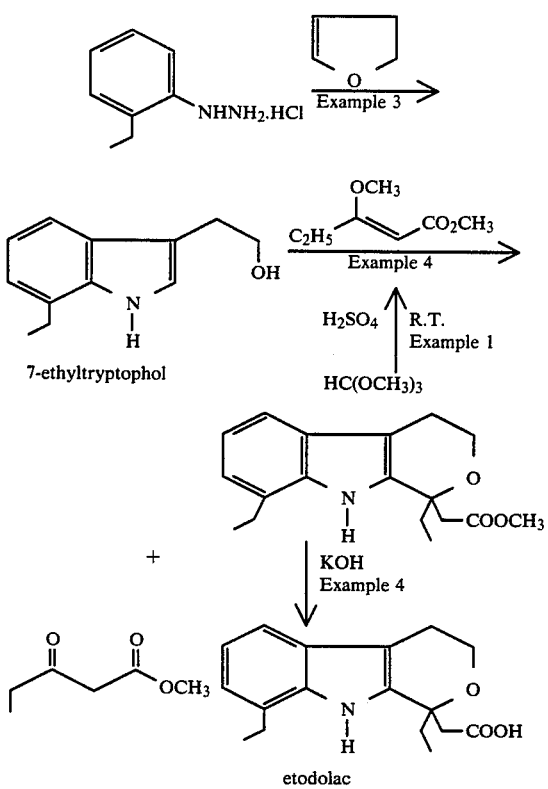

The following Examples will further illustrate this invention.

EXAMPLE 1

3-Methoxy-2-pentenoic Acid Methyl Ester

To a mixture of methyl propionylacetate (104 g. 0.8 mole) and trimethyl orthoformate 98% (95.3 g, 0.88 mole) was added dropwise 1 ml of concentrated H$_2$SO$_4$ at room temperature and it was allowed to stir overnight. After neutralization with excess anhydrous K$_2$CO$_3$, the solution was filtered and distilled to yield the title ester, b.p. 55° C. (0.55 mm).

EXAMPLE 2

2-Ethylphenylhydrazine Hydrochloride

A vigorously stirred solution of 487 ml concentrated hydrochloric acid and 218 ml of water at 0° C. was treated dropwise with 1.93 moles (234 g) of 2-ethylaniline. To the resulting thick suspension was added a solution of sodium nitrite (143 g, 2.07 moles) in 218 ml of water over 1.5 hours while maintaining the internal temperature between 8° C. and 14° C. Next, a solution of SnCl$_2$.2H$_2$O (4.37 moles, 985 g) in 1.312 l of 1:1 concentrated hydrochloric acid:water was added over 5 hours while the internal temperature was kept between 5° C. and 10° C. After 15 hours, the solid was collected on a filter paper and boiled in 1.2 l of water with decolorizing carbon. The solution was filtered through Celite, treated with 400 ml of concentrated hydrochloric acid and put in an ice bath for 0.5 hours. The tan plates were filtered and dried in vacuo over phosphorous pentoxide for 24 hours affording title compound, m.p. 181°–183° C.

NMR (D₂O): 1.039 (t,J=7.61, 3H, CH₃), 2.45 (q,J=7.61, 2H, CH₂) 4.630 (HOD, reference), 7.018–7.194 (m, 4H, aromatics).

EXAMPLE 3

7-Ethyltryptophol 2,3-Dihydropyran (2.2 g, 0.0314 mol) was added dropwise over 0.25 hours to a stirred mixture of 2-ethylphenylhydrazine hydrochloride (5.0 g, 0.03 mol), dioxane (40 ml) and water (1.8 ml) at room temperature. After the addition was complete the mixture was heated at 95° C. for 4 hours, cooled, diluted with diethyl ether and decanted. The ethereal phase was dried (MgSO₄), filtered, and concentrated to give 4.3 g of oil. Flash chromatography using 40% ethyl acetate in hexane as an eluant gave the title compound.

| NMR (CDCl₃): | # of protons | type | chemical shift (δ) |
|---|---|---|---|
| | 3 | CH₃ | 1.3 (t, J = 7) |
| | 1 | OH | 1.8 (bs, OH) |
| | 2 | CH₂CH₃ | 2.85 (q, J = 7) |
| | 2 | =CCH₂ | 3.0 (t, J = 6.5) |
| | 2 | CH₂O | 3.9 (t, J = 6.5) |
| | 4 | aromatic | 7.3 (m) |
| | 1 | NH | 8.1 (bs) |

EXAMPLE 4

1,8-Diethyl-1,3,4,9-tetrahydropyrano[3,4-b]indole-1-acetic Acid. Etodolac

A mixture consisting of 7-ethyltryptophol (3.8 g, 0.02 mol), 3-methoxy-2-pentenoic acid, methyl ester (7 ml), dichloromethane (100 ml) and boron trifluoride etherate (0.2 ml) was stirred at room temperature for 2.5 hours. The solution was washed twice with 5% aqueous sodium bicarbonate, water, dried (MgSO₄), filtered, and concentrated to give 9.7 g of an oil that solidified on standing. This was dissolved in methanol (30 ml), and a solution of potassium hydroxide (6.5 g, 0.12 mol) in water (5 ml) added. The solution was refluxed for 3 hours, cooled, concentrated and diluted with 20 ml water. The aqueous solution was washed twice with diethyl ether, acidified with 6N HCl and extracted twice with chloroform. The combined chloroform extracts were washed with water, dried (MgSO₄) filtered, and concentrated to give the title compound as an oil that solidified on standing. Recrystallization was from benzene-petroleum ether, m.p. 146°–147° C.

The useful antiinflammatory and analgesic activities of etodolac may be demonstrated by standard pharmacological tests. The antiinflammatory activity may be demonstrated by the Preventive Adjuvant Edema test described in J. Wax, et al., J. Pharmacol. Exp. Ther., 192, 166–171 (1975). The analgesic activity may be demonstrated by the Effects on Phenylquinone-Induced Writhing in Mice test described in E. Siegmund et al., Proc. Soc. Exp. Biol. Med., 95, 729–731 (1957).

Typical results obtained with these tests are:

| Preventive Adjuvant-Edema | |
|---|---|
| compound | ED₅₀ mg/kg, p.o. |
| etodolac | 4 |
| aspirin | 184 |
| Drug Effects Phenyquinone-Induced Writing in Mice | |
| compound | antinociceptive ED₅₀ mg/kg, p.o. |
| etodolac | 154 |
| aspirin | 54 |

Further tests for demonstrating the utility of etodolac are found in U.S. Pat. No. 3,939,178. The formulation and dose of etodolac to be used in the treatment of inflammation and pain are also set forth in U.S. Pat. No. 3,939,178.

We claim:

1. A process for preparing the compound 1,8-diethyl-1,3,4,9-tetrahydropyrano[3,4-b]indole-1-acetic acid of the formula

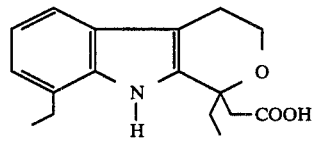

comprising reacting the compound 7-ethyltryptophol of formula

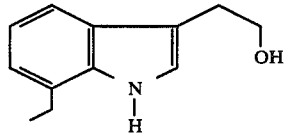

with 3-methoxy-2-pentenoic acid, methyl ester of formula

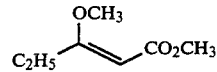

and hydrolyzing the ester with base.

2. The process according to claim 1 wherein the reaction of 7-ethyltryptophol with 3-methoxy-2-pentenoic acid, methyl ester is carried out in the presence of boron trifluoride etherate.

3. The process according to claim 2 wherein a mixture consisting of 7-ethyltryptophol, 3-methoxy-2-pentenoic acid, methyl ester and boron trifluoride etherate are stirred in dichloromethane solvent.

4. The process according to claim 3 wherein stirring is carried out at room temperature for about 2.5 hours.

* * * * *